(12) United States Patent
Koh et al.

(10) Patent No.: US 8,519,161 B2
(45) Date of Patent: Aug. 27, 2013

(54) PROCESS FOR PREPARING FLUOROPROPYLENE CARBONATE

(75) Inventors: Meiten Koh, Settsu (JP); Michiru Kagawa, Settsu (JP); Akiyoshi Yamauchi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 435 days.

(21) Appl. No.: 13/002,002

(22) PCT Filed: May 26, 2009

(86) PCT No.: PCT/JP2009/059585
§ 371 (c)(1),
(2), (4) Date: Dec. 29, 2010

(87) PCT Pub. No.: WO2010/001673
PCT Pub. Date: Jan. 7, 2010

(65) Prior Publication Data
US 2011/0118485 A1    May 19, 2011

(30) Foreign Application Priority Data
Jun. 30, 2008   (JP) .................................. 2008-171296

(51) Int. Cl.
*C07D 317/36* (2006.01)
(52) U.S. Cl.
USPC ....................................................... 549/229
(58) Field of Classification Search
USPC ....................................................... 549/229
See application file for complete search history.

(56) References Cited

U.S. PATENT DOCUMENTS

| | | | |
|---|---|---|---|
| 5,750,730 | A | 5/1998 | Nakano et al. |
| 2005/0075506 | A1 | 4/2005 | Handa et al. |
| 2006/0089514 | A1 | 4/2006 | DiMagno et al. |

FOREIGN PATENT DOCUMENTS

| | | |
|---|---|---|
| DE | 19700656 A1 | 7/1997 |
| EP | 0252393 A2 | 1/1988 |
| EP | 0775701 A1 | 5/1997 |
| JP | 60-100571 A | 6/1985 |
| JP | 9-286785 A | 11/1997 |
| JP | 10-233345 A | 9/1998 |
| RU | 2228933 C1 | 5/2004 |

OTHER PUBLICATIONS

Haoran Sun, et al.; "Anhydrous Tetrabuylammonium Fluoride"; Journal of the American Chemical Society (JACS Communications); vol. 127; No. 7; 2005; pp. 2050-2051; XP-002654064.
Kazuhide Tani, et al; "Preparation of optically active peralkyldiphosphines and their use, as the rhodium(I) complex, in the asymmetric catalytic hydrogenation of ketones"; Journal of Organometallic Chemistry; vol. 370; Jan. 1, 1989; pp. 203-221; XP-000982420.
Office Action issued Feb. 8, 2012 for counterpart RU Appln. No. 2011103166.
G. Mitschenko and K. Vatsuro; "Sinteticheskie metody organicheskoy khimii"; 1982; izd. Chimiya, p. 383.
K.K. Ingold; "Mekhanism reaktsiey I stroeniya organocheskih soedineniy"; 1959; M. izd. I-L; pp. 315-317.
Jikken Kagaku Koza 4th edition: Maruzen Co., Ltd.: Jun. 5, 1992; pp. 378-394.

*Primary Examiner* — Bernard Dentz
(74) *Attorney, Agent, or Firm* — Sughrue Mion, PLLC

(57) ABSTRACT

There is provided a process for preparing a fluoropropylene carbonate safely at high yield by one step (one pot), and the process is characterized by allowing a fluorinating agent to act on a propylene carbonate derivative having a group to be released in a fluorination reaction.

8 Claims, No Drawings

PROCESS FOR PREPARING FLUOROPROPYLENE CARBONATE

TECHNICAL FIELD

The present invention relates to a process for preparing a fluoropropylene carbonate.

BACKGROUND ART

A fluoropropylene carbonate is used as a solvent for a non-aqueous electrolytic solution to be used for electrochemical devices such as secondary batteries and capacitors.

This fluoropropylene carbonate, especially 3-fluoropropylene carbonate is prepared by the following methods.

(1) Method according to a reaction of a fluorine-containing compound having epoxy group (1-fluoro-2,3-epoxypropane) and carbon dioxide (Non-patent Documents 1 and 2)

(2) Method of direct fluorination of a propylene carbonate using fluorine gas (Non-patent Documents 3 to 5)

PRIOR ART DOCUMENTS

Non-Patent Documents

Non-patent Document 1: Chemistry—A European Journal, 12, pp. 1004-1015 (2006)

Non-patent Document 2: Journal of Organic Chemistry, 70, pp. 8583-8586 (2005)

Non-patent Document 3: Electrochemistry, 76, pp. 2-15 (2008)

Non-patent Document 4: Chemistry Letters, 37, pp. 476-477 (2008)

Non-patent Document 5: The Electrochemical Society of Japan, Proceedings of 75th Meeting, p. 106 (2008)

DISCLOSURE OF INVENTION

Problem to be Solved by the Invention

It is an object of the present invention to provide a process for preparing a fluoropropylene carbonate safely at high yield by using a fluorinating agent.

Means to Solve the Problem

The present invention relates to a process for preparing a fluoropropylene carbonate represented by the formula (2):

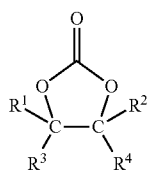

wherein $R^1$, $R^2$, $R^3$ and $R^4$ are the same or different and each is H or —$CH_2F$; at least one of $R^1$, $R^2$, $R^3$ and $R^4$ is —$CH_2F$, by allowing a fluorinating agent to react with a propylene carbonate derivative represented by the formula (1):

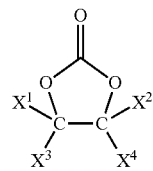

wherein $X^1$, $X^2$, $X^3$ and $X^4$ are the same or different and each is hydrogen atom or —$CH_2Y$ (Y is a group other than hydrogen atom and is released in fluorination reaction); at least one of $X^1$, $X^2$, $X^3$ and $X^4$ is —$CH_2Y$.

The fluorinating agent is preferably hydrofluoric acid, a salt of hydrofluoric acid, fluorine gas or a compound represented by the formula: MF, where M is an alkali metal atom or a quaternary ammonium cation.

The group Y (releasable group) released in the fluorination reaction is preferably chlorine atom, —OH or —$OSO_2R$, where R is an aliphatic or aromatic hydrocarbon group which may contain halogen atom, nitrogen atom or oxygen atom.

The preparation process of the present invention is suitable for preparing 3-fluoropropylene carbonate represented by the formula (2-1):

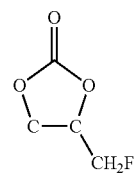

wherein the propylene carbonate derivative represented by the formula (1) is 3-Y-substituted propylene carbonate represented by the formula (1-1):

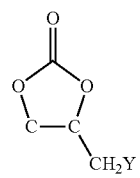

wherein Y is as defined above.

Effect of the Invention

According to the preparation process of the present invention, the fluoropropylene carbonate can be prepared safely at high yield by one step (one pot).

EMBODIMENT FOR CARRYING OUT THE INVENTION

In the process for preparing the fluoropropylene carbonate represented by the formula (2):

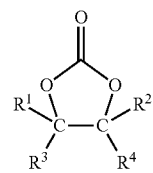

wherein $R^1$, $R^2$, $R^3$ and $R^4$ are the same or different and each is H or —$CH_2F$; at least one of $R^1$, $R^2$, $R^3$ and $R^4$ is —$CH_2F$, the fluorination reaction can be selectively conducted efficiently and the fluoropropylene carbonate can be prepared safely at high yield by substituting one of hydrogen atoms of —$CH_3$ of the propylene carbonate derivative as a starting material with a group which can be easily released when the fluorinating agent acts on it.

The starting material used in the present invention is the propylene carbonate derivative represented by the formula (1):

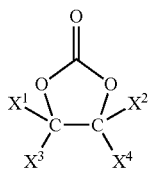

wherein $X^1$, $X^2$, $X^3$ and $X^4$ are the same or different and each is hydrogen atom or —$CH_2Y$ (Y is a group other than hydrogen atom and is released in the fluorination reaction); at least one of $X^1$, $X^2$, $X^3$ and $X^4$ is —$CH_2Y$.

The plural number or all of $X^1$, $X^2$, $X^3$ and $X^4$ may be —$CH_2Y$, and 3-Y-substituted propylene carbonate having one —$CH_2Y$ is preferred from the viewpoint of low viscosity when used as a solvent for a non-aqueous electrolytic solution.

The releasable group Y may be a group which is easily released when allowing the fluorinating agent to act on it and is replaced by fluorine atom. Examples of preferred releasable group Y are chlorine atom, —OH or —$OSO_2R$, where R is an aliphatic or aromatic hydrocarbon group which may contain halogen atom, nitrogen atom or oxygen atom, preferably a hydrocarbon group having 1 to 8 carbon atoms. Examples of R are alkyl groups which have 1 to 4 carbon atoms and may have fluorine atom such as —$CH_3$, —$CH_2CH_3$, —$CH(CH_3)_2$, —$CH_2CH_2CH_3$, —$C(CH_3)_3$, —$CH_2CH(CH_3)_2$, —$CH_2CH_2CH_2CH_3$, —$CF_3$, —$CF_2CF_3$, —$CF(CF_3)_2$, —$CF_2CF_2CF_3$, —$C(CF_3)_3$, —$CF_2CF(CF_3)_2$ and —$CF_2CF_2CF_2CF_3$; and aryl groups such as

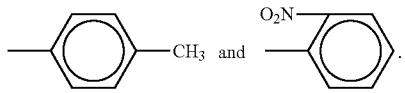

When there are plural releasable groups Y, they may be the same or different, but it is preferable that they are the same since the reaction easily proceeds due to the same reactivity.

Known fluorinating agents can be used, and examples thereof are hydrofluoric acid, salts of hydrofluoric acid, fluorine gas and a compound represented by the formula: MF, where M is an alkali metal atom or a quaternary ammonium cation.

Examples of a salt of hydrofluoric acid are amine hydrofluorides such as triethylamine monohydrofluoride.

Examples of a compound represented by MF are metallic fluorides such as KF, NaF, CsF and LiF; and compounds of quaternary ammonium cation and fluorine anion such as $(CH_3CH_2)_2NCF_2CFHCF_3$, $(CH_3CH_2)_2NSF_3$ and $CH_3CH_2CH_2CH_2N^+F^-$ (TBAF).

Among these, hydrofluoric acid, salts of hydrofluoric acid, fluorine gas and compounds represented by MF are preferred from the viewpoint of high reactivity, and especially compounds represented by MF are preferred from the viewpoint of easy handling.

A fluorinating agent acting on the releasable group Y is selected depending on kind of the releasable group Y and a fluorinating reaction scheme is decided. Some schemes are explained by means of examples of preparation of 3-fluoropropylene carbonate.

(Reaction Scheme 1)

Releasable group Y: —OH

Fluorinating agent: Compound of quaternary ammonium cation and fluorine anion (for example, $(CH_3CH_2)_2NCF_2CFHCF_3$)

Reaction Scheme:

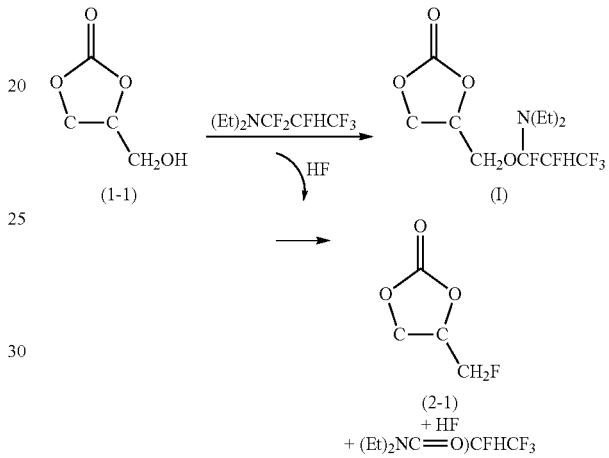

In this reaction, hydrofluoric acid generated by the reaction of a fluorinating agent with 3-hydroxypropylene carbonate (1-1) works to finally change the hydroxyl group at the third position of the propylene carbonate to fluorine. This reaction proceeds in one pot without isolation of an intermediate (I).

The intermediate (I) can be regarded as a starting material, and in that case, the releasable group Y is —$CF(N(CH_2CH_3)_2)(CFHCF_3)$ and the fluorinating agent is hydrofluoric acid (HF).

Examples of fluorination proceeding by this Reaction Scheme are those using $(CH_3CH_2)_2NSF_3$, $SF_4$, $SO_2F_2$ and $COF_2$ as a fluorinating agent.

Since this reaction is an exothermic reaction, it is preferable to conduct the reaction under cooling with ice with stirring. A reaction solvent is not required particularly, but when $(CH_3CH_2)_2NCF_2CFHCF_3$, $SF_4$, $SO_2F_2$, $COF_2$ or $(CH_3CH_2)_2NSF_3$ is used as a fluorinating agent, a polar solvent such as dichloromethane, chloroform, tetrahydrofuran, dimethylacetamide, dimethylformamide, glyme type solvents, acetonitrile, acetone, toluene or ethyl acetate may be used.

The reaction is completed in 1 to 10 hours, and a target 3-fluoropropylene carbonate (2-1) having purity (measured by GC) of 90 to 99% can be obtained at yield of 80 to 99%.

Here, synthesis of 3-hydroxypropylene carbonate (1-1) used as a starting material in this Reaction Scheme 1 is briefly explained below.

3-Hydroxypropylene carbonate (1-1) can be synthesized easily at high yield by a known method of allowing glycerin to react with carbon dioxide. Also, a method of allowing glycerin to react with phosgene (for example, JP6-9610A) and a method of allowing glycerin to react with ethylene carbonate by using aluminum oxide as a catalyst (for example, JP6-329663A) are known.

On the other hand, in the conventional method (1) for preparing fluoropropylene carbonate from a fluorine-containing compound having epoxy group, many steps for preparing, as a starting material, a fluorine-containing compound having epoxy group are required and a substance having strong toxicity is used, and therefore, there is a problem with yield and safety. Also, in the method (2) for fluorinating propylene carbonate directly with fluorine gas, since carbon atoms other than the carbon atom at the third position are also fluorinated, a lot of by-products are generated and therefore, there is a problem with yield and separation.

Accordingly, the preparation process of the present invention using 3-hydroxypropylene carbonate as a starting material is advantageous from the viewpoint of synthesis or availability of the starting material.

(Reaction Scheme 2)

Releasable group Y: —Cl, —OSO$_2$R, where R is an aliphatic or aromatic hydrocarbon group which may contain halogen atom, nitrogen atom or oxygen atom.

Fluorinating agent: Metallic fluorides (CsF, KF, NaF, LiF and the like), hydrofluoric acid (HF), salts of hydrofluoric acid Reaction Scheme:

[Structure: 3-Y-substituted propylene carbonate (1-2) with CH$_2$Y group → Fluorinating agent (CsF, HF or the like) → 3-fluoropropylene carbonate (2-1) with CH$_2$F group]

In this reaction, the fluorinating agent reacts directly with the releasable group at the third position of 3-Y-substituted propylene carbonate (1-2).

Examples of fluorination proceeding by this Reaction Scheme are those using CsF, KF, NaF, LiF, HF, (CH$_3$CH$_2$)$_3$N·m(HF) (m=1 to 3),

[Structure: pyridine·(HF)$_n$]

(n = 1 to 10)

and the like.

It is preferable to conduct this reaction at a reaction temperature of 50° to 150° C. with stirring. It is preferable to use a reaction solvent, and examples are polar solvents such as dichloromethane, chloroform, tetrahydrofuran, dimethylacetamide, dimethylformamide, glyme type solvents, acetonitrile, acetone, toluene and ethyl acetate.

The reaction is completed in 2 to 8 hours, and a target 3-fluoropropylene carbonate (2-1) having purity (measured by GC) of 90 to 99% can be obtained at yield of 70 to 99%.

Among 3-Y-substituted propylene carbonates (1-2) which are starting materials to be used in this Reaction Scheme 2, the compound having —OSO$_2$R as the releasable group Y can be easily synthesized, for example, by reacting a sulfonating agent (X—OSO$_2$R, where X is F, Cl, Br or I) such as alkylsulfonic acid halide or arylsulfonic acid halide with 3-hydroxypropylene carbonate of the formula (1-1).

[Structure: 3-hydroxypropylene carbonate with CH$_2$OH group → Sulfonating agent → carbonate with CH$_2$OSO$_2$R group]

Since this reaction is an exothermic reaction, it is preferable to conduct the reaction under cooling with ice with stirring. An organic solvent such as a polar solvent, for example, dichloromethane, chloroform, tetrahydrofuran, dimethylacetamide, dimethylformamide, glyme type solvents, acetonitrile, acetone, toluene or ethyl acetate may be used as a reaction solvent. It is also preferable to use a base such as triethylamine or pyridine as a catalyst.

The reaction is completed in 1 to 5 hours, and a target 3-Y-substituted propylene carbonate (1-2) having purity (measured by GC) of 90 to 99% can be obtained at yield of 80 to 99%.

Among 3-Y-substituted propylene carbonates (1-2) which are starting materials to be used in this Reaction Scheme 2, the compound having chlorine atom as the releasable group Y, namely, 3-chloropropylene carbonate can be easily synthesized by reaction of epichlorohydrin, CO$_2$ and LiBr in a polar solvent.

The fluoropropylene carbonate obtained by the preparation process of the present invention is used as an additive for a non-aqueous electrolytic solution of a lithium secondary battery and exhibits an effect of improving ionic conductivity and rate characteristics.

EXAMPLE

The preparation process of the present invention is then explained by means of examples, but the present invention is not limited to them.

Methods for analyses employed in the following examples are as follows.

(1) NMR
Equipment: AC-300 available from BRUKER
Measuring Conditions:
$^{19}$F-NMR: 282 MHz (trifluoromethylbenzene=−62.3 ppm)
$^1$H-MNR: 300 MHz (trifluoromethylbenzene=7.51 ppm)
(2) GC
GC-17A available from Shimadzu Corporation is used. DB624 column (length: 60 m, inner diameter: 0.32 mm, thickness: 1.8 mm) is used.

Example 1

[Structure: propylene carbonate with OH group → Et$_2$NCF$_2$CFHCF$_3$ / HF →]

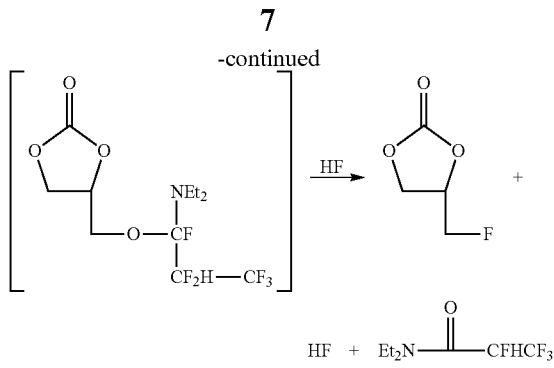

A reflux tube was mounted on the top of a 500 ml three-necked glass flask equipped with a stirrer, and a reactor was set so as to enable gases to be discharged through an alkali trap in a stream of nitrogen gas, and then, 100 g (850 mmol) of 3-hydroxypropylene carbonate was charged in the reactor, followed by stirring on ice bath. Then, thereto was added dropwise 190 g (850 mmol) of 1,1,2,3,3,3-hexafluoro-1-diethylaminopropane with a dropping funnel. At that time, heat generation of about 20° C. was confirmed. After confirming disappearing of the starting material by GC, the reaction was terminated. The stirring was continued for 24 hours. After the reaction, the reaction solution was subjected to extraction with dichloromethane, neutralization with an aqueous solution of saturated sodium bicarbonate and then distillation after drying of an organic layer with magnesium sulfate. Thus, 87 g (723 mmol) of a target product was obtained. According to the measurement with $^{19}$F-NMR and $^1$H-NMR, it was confirmed that the obtained target product was 3-fluoropropylene carbonate (yield: 85%, GC purity: 99.8%).

$^{19}$F-NMR: (heavy acetone): −237.6 to −237.0 ppm (1F)
$^1$H-NMR: (heavy acetone): 4.40 to 5.11 ppm (5H)

Example 2

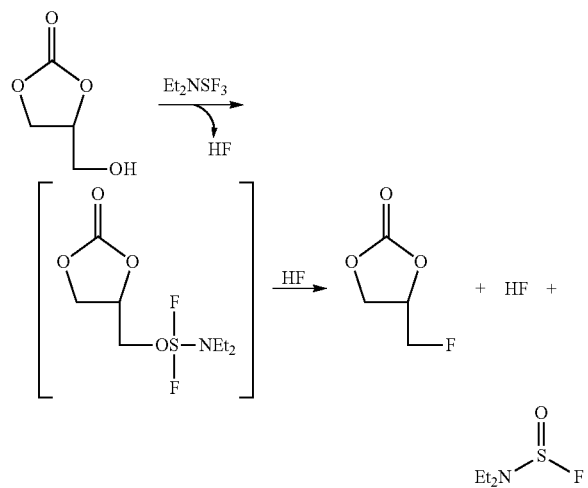

A reflux tube was mounted on the top of a 500 ml three-necked glass flask equipped with a stirrer, and a reactor was set so as to enable gases to be discharged through an alkali trap in a stream of nitrogen gas, and then, 100 g (850 mmol) of 3-hydroxypropylene carbonate and dichloromethane were charged in the reactor, followed by stirring at −78° C. Then, thereto was added dropwise 190 g (850 mmol) of diethylaminosulfur trifluoride with a dropping funnel. At that time, heat generation of about 20° C. was confirmed. After confirming disappearing of the starting material by GC, the reaction was terminated. The stirring was continued for two hours. After the reaction, the reaction solution was subjected to neutralization with a saturated aqueous solution of sodium bicarbonate and then distillation after drying of an organic layer with magnesium sulfate. Thus, 82 g (680 mmol) of a target product was obtained. According to the measurement with $^{19}$F-NMR and $^1$H-NMR, it was confirmed that the obtained product was 3-fluoropropylene carbonate (yield: 80%, GC purity: 99.5%).

$^{19}$F-NMR: (heavy acetone): −237.6 to −237.0 ppm (1F)
$^1$H-NMR: (heavy acetone): 4.40 to 5.11 ppm (5H)

Example 3

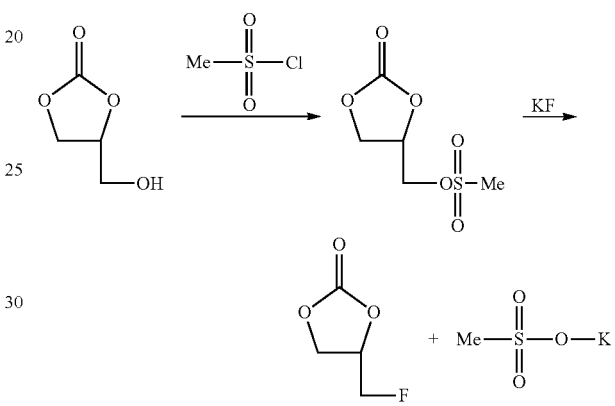

(First Stage)

A reflux tube was mounted on the top of a 500 ml three-necked glass flask equipped with a stirrer, and a reactor equipped with a nitrogen balloon was set, and then, 100 g (850 mmol) of 3-hydroxypropylene carbonate, 125 ml of tetrahydrofuran and 86 g (850 mmol) of triethylamine were charged in the reactor, followed by stirring on ice bath. Then, thereto was added dropwise 107 g (935 mmol) of methylsulfonic acid chloride with a dropping funnel. At that time, heat generation of about 20° C. was confirmed. After confirming disappearing of the starting material by GC, the reaction was terminated. The stirring of the reaction solution was continued for 24 hours. After the reaction, the reaction solution was subjected to quenching with 1N—HCl and after drying of a lower layer with magnesium sulfate, the obtained compound was used for the reaction at the second stage.

According to the measurement with $^1$H-NMR, it was confirmed that the obtained compound of the lower layer was 3-methylsulfonylpropylene carbonate (yield: 85%, 141 g (723 mmol)). $^1$H-NMR: (heavy acetone): 3.10 to 3.20 ppm (3H), 4.35 to 4.71 ppm (4H), 5.10 to 5.16 ppm (1H), (Second Stage)

A reflux tube was mounted on the top of a 500 ml three-necked glass flask equipped with a stirrer, and a nitrogen balloon was mounted to set a reactor, and then, 143 g (940 mmol) of cesium fluoride (CsF), 141 g (723 mmol) of 3-methylsulfonylpropylene carbonate obtained in the reaction of the first stage and 200 ml of diglyme were charged in the reactor, followed by stirring. Then the reactor was heated to 150° C., and stirring was continued until the starting material disappeared. The stirring was continued for two hours. After completion of the reaction, the reaction product was allowed to stand until its temperature reached room temperature, and then was diluted with ethyl acetate and the produced salt was filtrated, followed by washing with water, drying with magnesium sulfate and distillation to obtain 69 g (578 mmol) of a target product. According to the measurement with $^{19}$F-NMR and $^1$H-NMR, it was confirmed that the obtained product was 3-fluoropropylene carbonate.

The total yield by this two-staged reaction was 68%, and GC purity was 99.8%.

$^{19}$F-NMR: (heavy acetone): −237.6 to −237.0 ppm (1F)
$^1$H-NMR: (heavy acetone): 4.40 to 5.11 ppm (5H)

Example 4

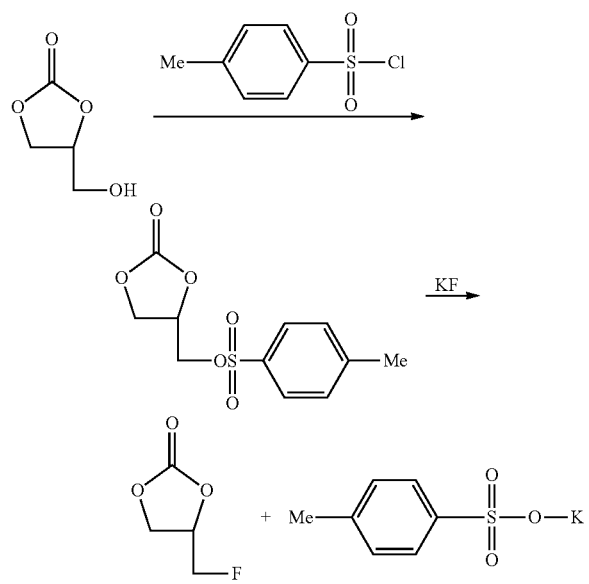

(First Stage)

A reflux tube was mounted on the top of a 500 ml three-necked glass flask equipped with a stirrer, and a reactor equipped with a nitrogen balloon was set, and then, 100 g (850 mmol) of 3-hydroxypropylene carbonate, 125 ml of tetrahydrofuran and 100 g (850 mmol) of triethylamine were charged in the reactor, followed by stirring on ice bath. Then, thereto was added dropwise 178 g (935 mmol) of p-toluenesulfonic acid chloride with a dropping funnel. At that time, heat generation of about 20° C. was confirmed. After confirming disappearing of the starting material by GC, the reaction was terminated. The stirring of the reaction solution was continued for 24 hours. After the reaction, the reaction solution was subjected to quenching with 1N—HCl and after drying of a lower layer with magnesium sulfate, the obtained compound was used for the reaction at the second stage.

According to the measurement with $^1$H-NMR, it was confirmed that the obtained compound of the lower layer was 3-(p-toluenesulfonyl)propylene carbonate (yield: 83%, 192 g (706 mmol)).

$^1$H-NMR: (heavy acetone): 2.25 to 2.34 ppm (3H), 4.35 to 4.71 ppm (4H), 5.15 to 5.20 ppm (1H), 7.23 to 7.82 ppm (4H)
(Second Stage)

A reflux tube was mounted on the top of a 500 ml three-necked glass flask equipped with a stirrer, and a nitrogen balloon was mounted to set a reactor, and then, 139 g (918 mmol) of cesium fluoride (CsF), 192 g (706 mmol) of 3-(p-toluenesulfonyl)propylene carbonate obtained in the reaction of the first stage and 200 ml of diglyme were charged in the reactor, followed by stirring. Then the reactor was heated to 150° C., and stirring was continued until the starting material disappeared. The stirring was continued for two hours. After completion of the reaction, the reaction product was allowed to stand until its temperature reached room temperature, and then was diluted with ethyl acetate and the produced salt was filtrated, followed by washing with water, drying with magnesium sulfate and distillation to obtain 68 g (565 mmol) of a target product. According to the measurement with $^{19}$F-NMR and $^1$H-NMR, it was confirmed that the obtained product was 3-fluoropropylene carbonate.

The total yield by this two-staged reaction was 66° A), and GC purity was 99.8%.

$^{19}$F-NMR: (heavy acetone): −237.6 to −237.0 ppm (1F)
$^1$H-NMR: (heavy acetone): 4.40 to 5.11 ppm (5H)

Example 5

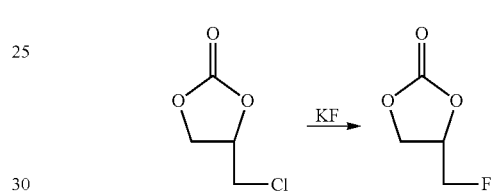

A reflux tube was mounted on the top of a 500 ml three-necked glass flask equipped with a stirrer, and a reactor equipped with a nitrogen balloon was set, and then, 116 g (850 mmol) of 3-chloropropylene carbonate and 64 g (1.11 mol) of potassium fluoride (KF) and 200 ml of diglyme were charged in the reactor, followed by stirring. Then the reactor was heated to 150° C., and stirring was continued until the starting material disappeared. The stirring was continued for two hours. After completion of the reaction, the reaction product was allowed to stand until its temperature reached room temperature, and then was diluted with ethyl acetate and the produced salt was filtrated, followed by washing with water, drying with magnesium sulfate and distillation to obtain 61 g (510 mmol) of a target product. According to the measurement with $^{19}$F-NMR and $^1$H-NMR, it was confirmed that the obtained product was 3-fluoropropylene carbonate (yield: 60%, GC purity: 99.5%).

$^{19}$F-NMR: (heavy acetone): −237.6 to −237.0 ppm (1F)
$^1$H-NMR: (heavy acetone): 4.40 to 5.11 ppm (5H)

Example 6

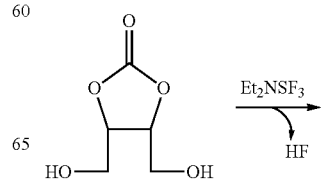

-continued

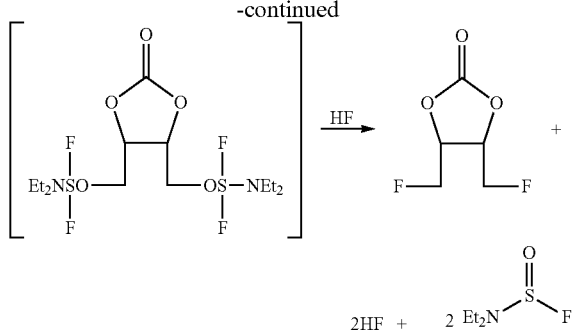

A reflux tube was mounted on the top of a 500 ml three-necked glass flask equipped with a stirrer, and a reactor was set so as to enable gases to be discharged through an alkali trap in a stream of nitrogen gas, and then, 63.1 g (425 mmol) of 3,4-di(hydroxymethyl)ethylene carbonate and dichloromethane were charged in the reactor, followed by stirring at −78° C. Then, thereto was added dropwise 190 g (850 mmol) of diethylaminosulfur trifluoride with a dropping funnel. At that time, heat generation of about 20° C. was confirmed. After confirming disappearing of the starting material by GC, the reaction was terminated. The stirring was continued for two hours. The reaction solution was subjected to neutralization with an aqueous solution of saturated sodium bicarbonate and then distillation after drying of an organic layer with magnesium sulfate. Thus, 51.7 g (340 mmol) of a target product was obtained. According to the measurement with $^{19}F$- and $^{1}H$-NMR, it was confirmed that the obtained product was 3,4-di(monofluoromethyl)ethylene carbonate (yield: 80%, GC purity: 99.5%).

$^{19}F$-NMR: (heavy acetone): −237.3 to −237.0 ppm (2F)
$^{1}H$-NMR: (heavy acetone): 4.40 to 5.00 ppm (4H)

Example 7

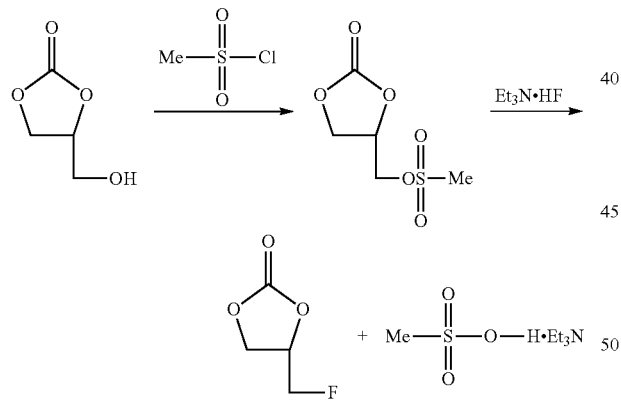

(First Stage)
A reflux tube was mounted on the top of a 500 ml three-necked glass flask equipped with a stirrer, and a reactor equipped with a nitrogen balloon was set, and then, 100 g (850 mmol) of 3-hydroxypropylene carbonate, 125 ml of tetrahydrofuran and 86 g (850 mmol) of triethylamine were charged in the reactor, followed by stirring on ice bath. Then, thereto was added dropwise 107 g (935 mmol) of methylsulfonic acid chloride with a dropping funnel. At that time, heat generation of about 20° C. was confirmed. After confirming disappearing of the starting material by GC, the reaction was terminated. The stirring of the reaction solution was continued for 24 hours. After the reaction, the reaction solution was subjected to quenching with 1N—HCl and after drying of a lower layer with magnesium sulfate, the obtained compound was used for the reaction at the second stage.

According to the measurement with $^{1}H$-1-NMR, it was confirmed that the obtained compound of the lower layer was 3-methylsulfonylpropylene carbonate (yield: 85%, 141 g (723 mmol)). $^{1}H$-NMR: (heavy acetone): 3.10 to 3.20 ppm (3H), 4.35 to 4.71 ppm (4H), 5.10 to 5.16 ppm (1H)

(Second Stage)
A reflux tube was mounted on the top of a 500 ml three-necked glass flask equipped with a stirrer, and a nitrogen balloon was mounted to set a reactor, and then, 141 g (723 mmol) of 3-methylsulfonylpropylene carbonate obtained in the reaction of the first stage, 114 g (940 mmol) of triethylamine monohydrofluoride and 200 ml of diglyme were charged in the reactor, followed by stirring. Then the reactor was heated to 150° C., and stirring was continued until the starting material disappeared. The stirring was continued for two hours. After completion of the reaction, the reaction product was allowed to stand until its temperature reached room temperature, and then was diluted with ethyl acetate and the produced salt was filtered, followed by washing with water, drying with magnesium sulfate and distillation to obtain 56.1 g (468 mmol) of a target product. According to the measurement with $^{19}F$- and $^{1}H$-NMR, it was confirmed that the obtained product was 3-fluoropropylene carbonate.

The total yield by this two-staged reaction was 65%, and GC purity was 99.8%.

$^{19}F$-NMR: (heavy acetone): −237.6 to −237.0 ppm (1F)
$^{1}H$-NMR: (heavy acetone): 4.40 to 5.11 ppm (5H)

The invention claimed is:
1. A process for preparing a fluoropropylene carbonate represented by the formula (2):

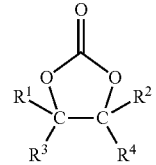

wherein $R^1$, $R^2$, $R^3$ and $R^4$ are the same or different and each is H or —$CH_2F$; at least one of $R^1$, $R^2$, $R^3$ and $R^4$ is —$CH_2F$, by allowing a fluorinating agent to react with a propylene carbonate derivative represented by the formula (1):

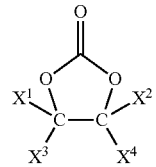

wherein $X^1$, $X^2$, $X^3$ and $X^4$ are the same or different and each is hydrogen atom or —$CH_2Y$ (Y is a group other than hydrogen atom and is released in fluorination reaction); at least one of $X^1$, $X^2$, $X^3$ and $X^4$ is —$CH_2Y$.

2. The preparation process of claim 1, wherein the fluorinating agent is hydrofluoric acid, a salt of hydrofluoric acid, fluorine gas or a compound represented by the formula: MF, where M is an alkali metal atom or a quaternary ammonium cation.

3. The preparation process of claim 1, wherein the group Y released in the fluorination reaction is chlorine atom, —OH or —$OSO_2R$, where R is an aliphatic or aromatic hydrocarbon group which may contain halogen atom, nitrogen atom or oxygen atom.

4. The preparation process of claim 1, wherein the propylene carbonate derivative represented by the formula (1) is 3-Y-substituted propylene carbonate represented by the formula (1-1):

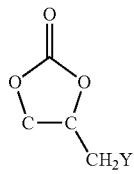

wherein Y is as defined above, and the fluorinated propylene carbonate represented by the formula (2) is 3-fluoropropylene carbonate represented by the formula (2-1):

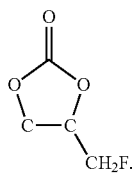

5. The preparation process of claim 2, wherein the group Y released in the fluorination reaction is chlorine atom, —OH or —OSO$_2$R, where R is an aliphatic or aromatic hydrocarbon group which may contain halogen atom, nitrogen atom or oxygen atom.

6. The preparation process of claim 2, wherein the propylene carbonate derivative represented by the formula (1) is 3-Y-substituted propylene carbonate represented by the formula (1-1):

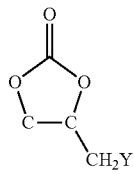

wherein Y is as defined above, and the fluorinated propylene carbonate represented by the formula (2) is 3-fluoropropylene carbonate represented by the formula (2-1):

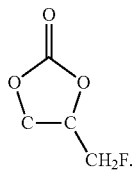

7. The preparation process of claim 3, wherein the propylene carbonate derivative represented by the formula (1) is 3-Y-substituted propylene carbonate represented by the formula (1-1):

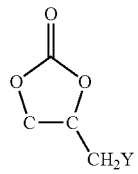

wherein Y is as defined above, and the fluorinated propylene carbonate represented by the formula (2) is 3-fluoropropylene carbonate represented by the formula (2-1):

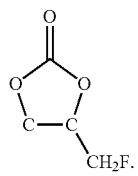

8. The preparation process of claim 5, wherein the propylene carbonate derivative represented by the formula (1) is 3-Y-substituted propylene carbonate represented by the formula (1-1):

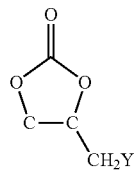

wherein Y is as defined above, and the fluorinated propylene carbonate represented by the formula (2) is 3-fluoropropylene carbonate represented by the formula (2-1):

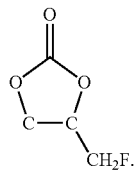

\* \* \* \* \*